United States Patent [19]
Goldberg et al.

[11] Patent Number: 6,027,932
[45] Date of Patent: Feb. 22, 2000

[54] METHODS OF IMPROVING VIABILITY OF CELLS AT LOW TEMPERATURE

[75] Inventors: Alfred L. Goldberg, Brookline; Olga Kandror, Newton, both of Mass.

[73] Assignee: President and Fellows of Harvard College, Cambridge, Mass.

[21] Appl. No.: 09/075,087

[22] Filed: May 8, 1998

Related U.S. Application Data

[60] Provisional application No. 60/046,064, May 9, 1997.

[51] Int. Cl.⁷ ........................................... C12N 9/90
[52] U.S. Cl. ................ 435/245; 435/4; 435/7.2; 435/325; 435/410; 435/233; 435/375
[58] Field of Search ................ 435/233, 4, 7.2, 435/325, 410, 245, 375

[56] References Cited

U.S. PATENT DOCUMENTS

| | | | |
|---|---|---|---|
| 5,428,131 | 6/1995 | Trent et al. | 530/350 |
| 5,470,971 | 11/1995 | Kondo et al. | 536/23.7 |
| 5,827,685 | 10/1998 | Lindquist | 435/69.1 |

OTHER PUBLICATIONS

Galat, 1993, "Peptidyl cis–trans–isomerases: immunophilins", *Eur. J. Biochem.*, 216(3): 689–707.

Guthrie and Wickner, 1990, "Trigger factor depletion or overproduction causes defective cell division but does not block protein export", *J. Bacteriol.*, 172(10): 5555–5526.

Jones, Van Bogelen and Neidhardt, 1987, "Induction of proteins in response to low temperature in *Escherichia coli*", *J. Bacteriol.*, 169(5): 2092–2095.

Jones, Cashel, Glaser and Neidhardt, 1992, *J. Bacteriol.*, "Function of a relaxed–like state following temperature downshifts in *Escherichia coli*", 174(12): 3903–3914.

Kandror, Sherman, Rhode and Goldberg, 1995, "Trigger factor is involved in GroEL–dependent protein degradation in *Escherichia coli* and promotes binding of GroEL to unfolded proteins", *EMBO J.*, 14(23): 6021–6027.

Kandror, Sherman, Moerschall and Goldberg, 1997, "Trigger factor associates with GroEL in vivo and promotes its binding to certain polypeptides", *J. Biol. Chem.*, 272(3): 1730–1734.

Ng, Ingraham and Mar, 1962, "Damage and derepression in *Escherichia coli* resulting from growth at low temperatures", *J. Bacteriol.*, 84: 331–339.

Rudd, Sofia, Koonin, Plunkett, Lazar and Rouviere, 1995, "A new family of peptidyl–prolyl isomerases", *Trends Biochem. Sci.*, 20(1): 12–14.

Van Bogelen and Neidhardt, 1990, "Ribosomes as sensors of heat and cold shock in *Escherichia coli*", *Proc. Natl. Acad. Sci. U.S.A.*, 87(15): 5589–5593.

*Primary Examiner*—Rebecca E. Prouty
*Assistant Examiner*—Richard Hutson
*Attorney, Agent, or Firm*—Banner & Witcoff, Ltd.

[57] ABSTRACT

Methods are disclosed which employ cold-shock proteins, such as Trigger Factor, to confer cold-tolerance to cells and to enhance viability of cells at temperatures at which the cells would not normally remain viable. Proteins having peptidyl-proline isomerase activity are also disclosed as being useful to confer cold-tolerance to cells. Cells which overexpress cold-shock proteins are useful in cell-based expression systems which are intended to express proteins at low temperatures.

4 Claims, 10 Drawing Sheets

FIG. 1

| FIG. 1A |
|---|
| FIG. 1B |
| FIG. 1C |
| FIG. 1D |

```
1        /                              31       /
CGT TCT CGA CTC ATA AAA GTG ATG CCG CTA TAA TGC cgc GTC CTA TTT GAA TGC TTT CGG
61       /                              91       /
GAT GAT TCT GGT AAC AGG GAA TGT GAT TGA TTA TAA GAA CAT CCC GGT TCC GGC GAA GCC
121      /                              151      /
AAC AAC CTG TGC TTG CGG GGT AAG AGT TGA CCG AGC ACT GTG ATT TTT TGA GGT AAC AAG
211      /
ATG CAA GTT TCA GTT GAA ACC ACT CAA GGC CTT GGC CGC CGT GTA ACG ATT ACT ATC GCT
met gln val ser val glu thr thr gln val gly leu gly arg arg val thr ile thr ile ala
241      /                              271      /
GCT GAC AGC ATC GAG ACC GCT GTT AAA AGC GAG CTG GTC AAC GTT GCG AAA AAA GTA CGT
ala asp ser ile glu thr ala val lys ser glu leu val asn val ala lys lys val arg
301      /                              331      /
ATT GAC GGC TTC CGC AAA GGC AAA GTG CCA ATG AAT ATC GTT GCT CAG CGT TAT GGC GCG
ile asp gly phe arg lys gly lys val pro met asn ile val ala gln arg tyr gly ala
```

```
361 /
TCT GTA CGC CAG GAC GTT CTG GGT GAC AGC CGT AAC TTC ATT GAC GCC ATT
ser val arg gln asp val leu gly asp ser arg asn phe ile asp ala ile
421 /                                  391 /
AAA GAA AAA ATC AAT CCG GCT GGC GCA CCG ACT TAT GTT CCG GGC GAA TAC AAG CTG GGT
lys glu lys ile asn pro ala gly ala pro thr tyr val pro gly glu tyr lys leu gly
481 /                                  451 /
GAA GAC TTC ACT TAC TCT GTA GAG TTT GAA GTT TAT CCG GAA GTT GAA CTC GAG GGT CTG
glu asp phe thr tyr ser val glu phe glu val tyr pro glu val glu leu glu gly leu
541 /                                  511 /
GAA GCG ATC GAA GTT GAA AAA CCG ATC GTT GAA GTG ACC GAC GCT GAC GTT GAC GGC ATG
glu ala ile glu val glu lys pro ile val glu val thr asp ala asp val asp gly met
601 /                                  571 /
CTG GAT ACT CTG CGT AAA CAG CAG GCG ACC TGG AAA GAA AAA GAC GGC GCT GTT GAA GCA
leu asp thr leu arg lys gln gln ala thr trp lys glu lys asp gly ala val glu ala
661 /                                  631 /
GAA GAC CGC GTA ACC ATC GAC TTC ACC GGT TCT GTA GAC GGC GAA GAG TTC GAA GGC GGT
glu asp arg val thr ile asp phe thr gly ser val asp gly glu glu phe glu gly gly
721 /                                  691 /
AAA GCG TCT GAT TTC GTA CTG GCG ATG GGC CAG CAG GGT CGT ATG ATC CCG GGC TTT GAA GAC
lys ala ser asp phe val leu ala met gly gln gln gly arg met ile pro gly phe glu asp
781 /                                  751 /
GGT ATC AAA GGC CAC AAA GGT ATC AAA GGC GAA GAG TTC CGC GGC GAA GAA
gly ile lys gly his lys ala gly glu glu phe thr ile asp val thr phe pro glu glu
                                       811 /
```

```
841  /
TAC CAC GCA GAA AAC CTG AAA GGT AAA GCA GCG AAA TTC GCT ATC AAC CTG AAG AAA GTT
tyr his ala glu asn leu lys gly lys ala ala lys phe ala ile asn leu lys lys val
901 /                                       871 /
                                            931 /
GAA GAG CGT GAA CTG CCG GAA CTG ACT GCA GAA TTC ATC AAA CGT TTC GGC GTT GAA GAT
glu glu arg glu leu pro glu leu thr ala glu phe ile lys arg phe gly val glu asp
961 /                                       991 /
GGT TCC GTA GAA GGT CTG CGC GCT GAA GTG CGT AAA AAC ATG GAG CGC GAG CTG AGA GCG
gly ser val glu gly leu arg ala glu val arg lys asn met glu arg glu leu arg ala
1021 /                                      1051 /
CCA TCC GTA ACC GCG TTA AGT TCT CAG GCG CTG ATC GAA GGT CTG GTA AAA GCT AAC GAC ATC
pro ser val thr ala leu ser ser gln ala leu ile glu gly leu val lys ala asn asp ile
1081 /                                      1111 /
GAC GTA CCG GCT GCG CTG ATC GAC AGC GAA GTT CTG CGT CGC,CAG GCT GCA GCA CAG
asp val pro ala ala leu ile asp ser glu val leu arg arg gln ala ala ala gln
1141 /                                      1171 /
CGT TTC GGT GGC AAC GAA AAA CAA GCT CTG CAA CTG GAA CTG TTC GAA GAA CAG
arg phe gly gly asn glu lys gln ala leu gln leu glu leu phe glu glu gln
1201 /                                      1231 /
GCT AAA CGC CGC GTA GTT GGT CTG CTG CTG GGC GAA GTT ATC CGC ACC AAC GAG CTG
ala lys arg arg val val gly leu leu leu gly glu val ile arg thr asn glu leu
1261 /                                      1291 /
AAA GCT GAC GAA GAG CGC GTG AAA GGC GTG AAA GAG ATG GCT TCT GCG TAC GAA GAT
lys ala asp glu glu arg val lys gly val lys glu met ala ser ala tyr glu asp
```

FIG. 1C

```
1321 /
CCG AAA GAA GTT ATC GAG TTC TAC AGC AAA GAA AAC CTG ATG GAC AAC ATG CGC AAT
pro lys glu val ile glu phe tyr ser lys glu asn leu met asp asn met arg asn
       1381 /                                         1411 /
GTT GCT CTG GAA GAA CAG GCT GTT GAA GCT CTG GCG AAA GCG AAA GTG ACT GAA AAA
val ala leu glu glu gln ala val glu ala leu ala lys ala lys val thr glu lys
             1441 /                      *            1471 /
GAA ACC ACT TTC AAC GAG CTG ATG AAC CAG CAG GCG TAA TTT ACG CAG CAT AAC GCG CTA
glu thr thr phe asn glu leu met asn gln gln ala OCH phe thr gln his asn ala leu
       1501 /                                         1531 /
AAT TCG CAC AAA GGC CCG TCA CCG CCA GGT GGT CTT TTT TTT GTC ATG AAT TTT GCA
asn ser his lys gly pro ser pro pro gly gly leu phe phe val met asn phe ala
             1561 /                                         1591 /
TGG AAC CGT GCG AAA AGC CTC TTT CGG TGT TAG TGT AAC AAA AGA TTG TTA TGC TTG
trp asn arg ala lys ser leu phe arg cys AMB cys asn lys asn arg leu leu cys leu
       1621 /                                         1651 /
AAA TAT GGT GAT GCC GTA CCC ATA ACA CAG GGA CTA GCT GAT AAT CCG TCC ATA AGG TTA
lys tyr gly asp ala val pro ile thr gln gly leu ala asp asn pro ser ile arg leu
             1681 /                                         1711 /
CAA TCG GTA CAG CAG GTT TTT TCA ATT TTA TCC AGG AGA CGG AAA TGT CAT ACA GCG GCG
gln ser val gln gln val phe ser ile leu ser arg arg arg lys cys his thr ala ala
       1741 /                                         1771 /
AAC GAG ATA ACT TTG CAC CCC ATA TGG CGC TGG TGC CGA TGG TCA TTG AAC AGA CCT CCA
asn glu ile thr leu his pro ile trp arg trp cys arg trp ser leu asn arg pro pro
             1801 /
CGC GGT GAG
arg gly glu
```

FIG. 1D

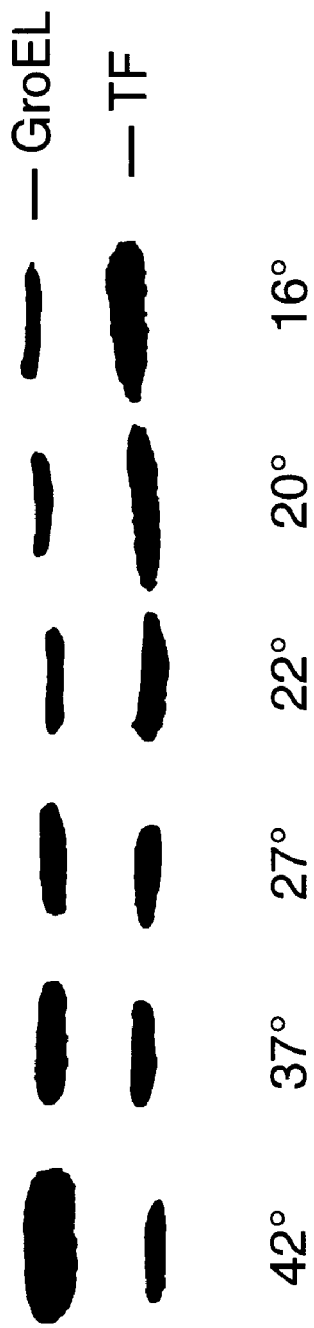
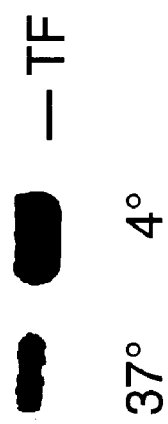

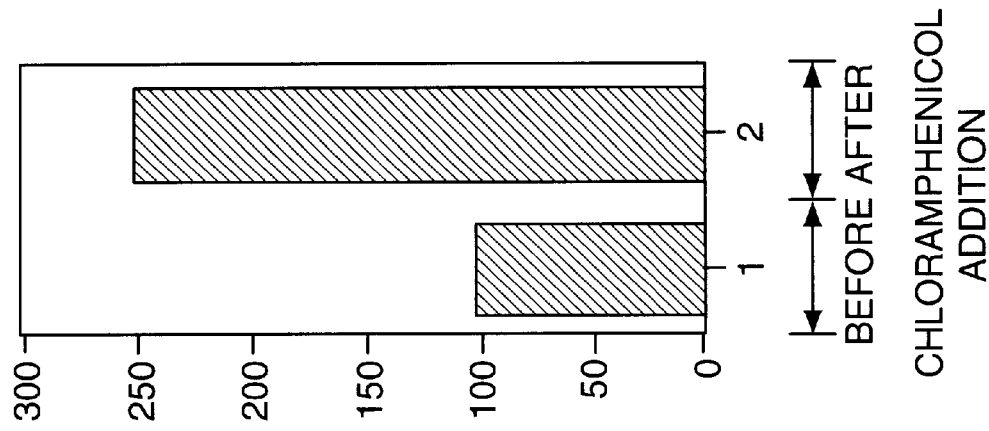
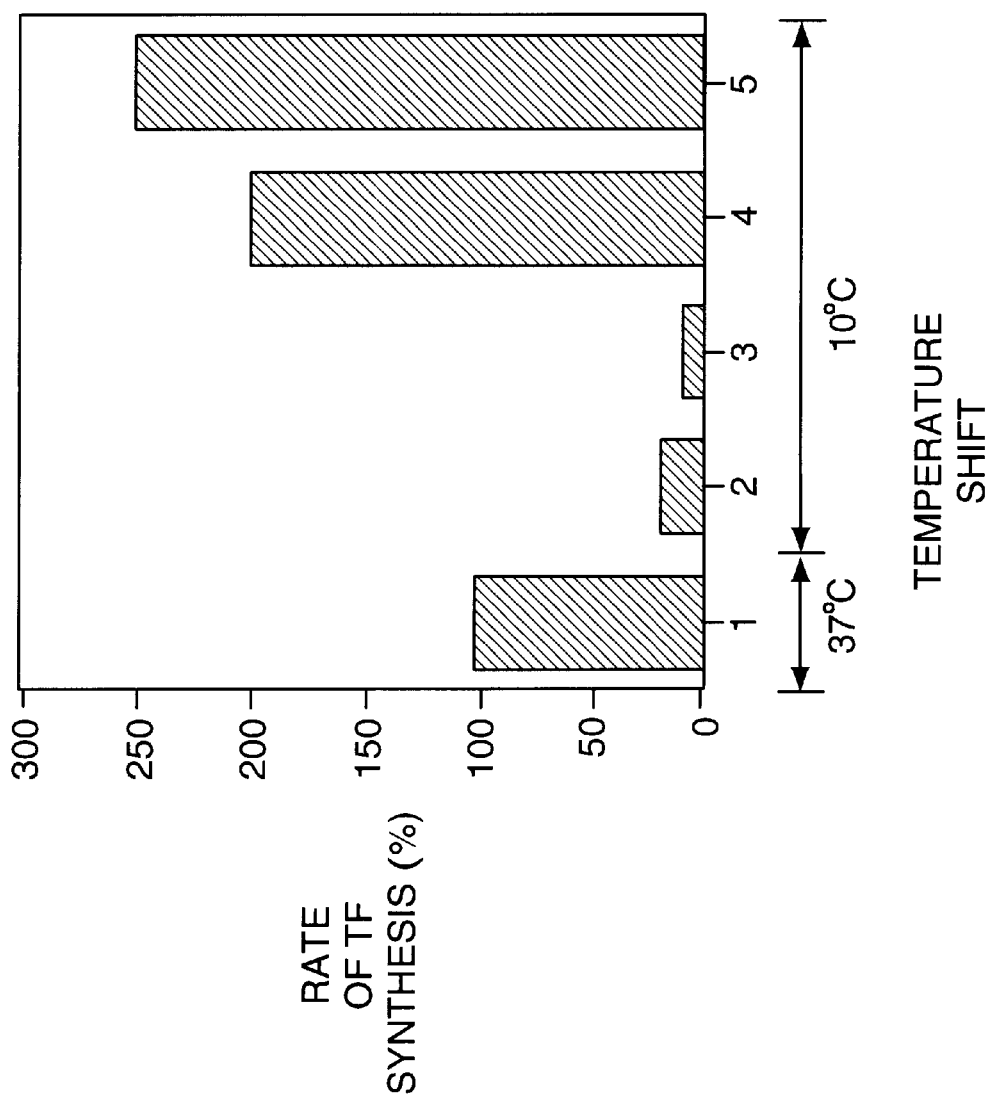
FIG. 3A
FIG. 3B

N, Amino-terminal TF fragment
MRGSHHHHHH GSDDDDK Met1 - Arg 145 in pQE30

M, TF PPIase domain
MRGSHHHHHH GSDDDDK Met145 - Glu 251 in pQE30

C, Carboxy-terminal TF fragment
GSTLVPR GSDDDDK Glu 251 - Ala 432 in pGEX-KG

FIG. 8

METHODS OF IMPROVING VIABILITY OF CELLS AT LOW TEMPERATURE

This application claims the benefit of U.S. Provisional Application No. 60/046,064, filed May 9, 1997.

This invention was supported by NIH Grant No. GM51923-02 and the government has certain rights to the invention.

BACKGROUND OF THE INVENTION

1. Field of the Invention

Embodiments of the present invention relate to the field of biotechnology. More particularly, embodiments of the present invention relate to proteins and cells expressing such proteins which are useful in prolonging cell viability at temperatures where the rate of cell growth is reduced or prevented leading to eventual cell death. Cells are induced or genetically altered to overexpress cold-shock proteins and to enhance viability under low temperature conditions at which cell death normally occurs.

2. Description of Related Art

It is known that when certain cells are exposed to sudden changes in temperature that are either higher or lower than normal physiological temperatures, synthesis of specific proteins may be induced. When eukaryotic or prokaryotic cells are exposed to increases in temperature (termed "heat shock"), a shift occurs from the pattern of synthesis of normal cellular proteins to enhance the synthesis of a group of cell proteins commonly termed "heat-shock" proteins. Likewise, when certain cells (e.g. bacteria) are exposed to decreases in temperature, a class of proteins termed "cold-shock" proteins are synthesized at increased rates. It has been shown that a heat-shock response is induced to help protect the cell from otherwise lethal high temperatures. A number of these heat-shock proteins are molecular chaperones which can assist in refolding or degradation of heat-damaged cell proteins, and others are proteases or other components of the cell's proteolytic machinery which help the cell's ability to destroy the heat-damaged proteins.

Proteins have been identified as being produced at increased differential rates relative to other proteins upon the shifting of an *E. coli.* culture from ambient temperatures of 37° C. to 10° C. and lower, and have been termed "cold shock" proteins. See, Jones, P. G., VanBogelen, R. A., and Neidhardt, F. C. (1987) *Journal of Bacteriology* 169(5), 2092–2095; and Jones, P. G., Cashel, M., Glaser, G., and Neidhardt, F. C. (1992) *Journal of Bacteriology* 174(12), 3903–3914, each hereby incorporated by reference in their entirety. Some of the proteins are known to be involved in RNA transcription and translation, however, no specific in vivo beneficial effect of induction of the cold-shock proteins has been demonstrated.

Identification of proteins which prolong the life of the cell under conditions which the cell normally would not grow and would not remain viable is of major scientific and practical utility. Cells having this desirable characteristic would enable cell-based expression systems normally capable of operating only at room temperatures to operate at lower temperatures where certain proteins are produced more efficiently, in greater quantity or in greater activity. Such cell-based expression systems would advantageously be capable of expressing certain proteins which may undergo improper folding or degradation at higher temperatures, and so cannot be expressed at room temperatures.

Altering a cell to express proteins which enhance the cold-resistance characteristic of the cell is also advantageous in the field of agriculture to protect plants against frost or injury due to sudden low temperature; for production of food products, and any other biological (or pharmaceutical) products that should be protected from a harsh or stress-creating situation like extreme low temperatures. In addition, enhancing viability of mammalian cells at low temperatures may also be useful in cells or organ preservation, for example, where it is necessary to store the cell or organ prior to transplantation. Accordingly, the identification of proteins capable of enhancing or promoting cell viability at low temperatures where cell growth is greatly reduced or prevented and which lead to cell death and methods of altering cells to enhance their viability is of important scientific and commercial utility.

Trigger Factor ("TF") is an abundant protein in *E. coli.* whose in vivo importance has remained unclear for a long time. The amino acid sequence and corresponding DNA sequence has been determined and is shown in FIG. 1. See also Guthrie, B., and Wickner, W. (1990) *Journal of Bacteriology* 172(10), 5555–5562 hereby incorporated by reference in its entirety. It was originally isolated as a factor that bound to proOmpA protein and promoted its translocation into membrane vesicles in vitro. However, subsequent studies failed to demonstrate any role of TF in protein secretion in vivo. Recently, however, TF has been shown to have a number of remarkable properties including possible function as a molecular chaperone that promotes the folding of nascent polypeptides. TF is tightly associated with the 50S ribosomal particle and can be cross-linked to nascent polypeptide chains. In addition, TF was recently shown to be one of several *E. coli.* peptidyl-prolyl isomerases (PPI) that can catalyze the cis/trans isomerization of Xaa-Pro peptide bonds in polypeptides (PPI activity). This reaction is often a rate-limiting step in the folding of certain polypeptides, such as RNAseT1, especially at low temperatures.

TF has been shown to function together with the major chaperones, GroEL and GroES, in the selective degradation of certain polypeptides. See Kandror, O., Sherman, M., Rhode, M., and Goldberg, A. L. (1995) *EMBO Journal* 14(23), 6021–27. TF has also been shown to be a regulator of GroEL function. See Kandror, O., Sherman, M., Moerschall, R., and Goldberg, A. L. *Journal of Biological Chemistry*. A fraction of the cell's TF is associated with GroEL and these GroEL-TF complexes show much higher affinity for many unfolded proteins. Moreover, the addition of purified TF to GroEL in vitro increases GroEL's binding capacity for these proteins. This enhancement of GroEL binding can account for its ability to stimulate the degradation of certain proteins but may also be important in promoting protein folding.

Despite these seemingly important biochemical effects, increasing or decreasing TF levels was found not to affect growth rate or to have marked physiological consequences at 37° C. The only clear in vivo effect was an increase in filamentation and mucoidity which was seen when TF levels were either increased or reduced. See Guthrie, B., and Wickner, W. (1990) *Journal of Bacteriology* 172(10), 5555–5562.

By contrast, the major molecular chaperones in *E. coli.* (e.g. Dna K and its cofactors, GroEL and GroES) are essential factors for normal growth at 37 ° C. They are also heat-shock proteins that are induced at high temperatures and by other conditions that cause damage to cell proteins. These chaperones prevent protein aggregation, help catalyze protein refolding, and can promote the selective degradation of heat-damaged polypeptides. Cells that fail to generate major heat-shock proteins are not able to grow at normal temperatures and die rapidly during heat-shock.

Unlike most molecular chaperones, TF is not a heat-shock protein and is not essential for viability at high temperatures. On the contrary, it has been demonstrated that the effects of TF on protein degradation (Kandror, O., Sherman, M., Rhode, M., and Goldberg, A. L. (1995) *EMBO Journal* 14(23), 6021–6027 hereby incorporated by reference in its entirety) and on GroEL's binding to proteins were much greater when cells were grown at 20° C. than at 37° C.

Despite attempts to elucidate the physiological importance of TF, the art provides no indication of whether TF is a cold-shock protein or what effect it may have in cells subjected to low temperatures where cell viability is decreased. Accordingly, a need exists to explore the nature of protein production induced by low temperatures at which cells normally would not grow and would not remain viable and to discover methods of increasing cell viability at such low temperatures.

SUMMARY OF THE INVENTION

Embodiments of the present invention are based on the discovery that cold-shock proteins are useful in methods of making cells cold-resistant and in enhancing cell viability at low temperatures. "Low temperatures" are defined herein as temperatures at which rapid cell growth is prevented and at which cells grow very slowly if at all and do not remain viable over time, i.e. cells die at a steady rate as a result of the low temperature, and fewer cells remain viable with time. Low temperatures, for example, typically include those between 0° C. and 10° C. It is to be understood, however, that different cell types may react differently to different low temperatures whether below 0° C. or above 10° C. and have different death rates. It is therefore contemplated that the methods of the present invention will advantageously be applied to enhance the viability of cells at all low temperatures where a particular cell would not otherwise remain viable over time. It is to be further understood that the term "cold-shock protein" includes naturally occurring cold-shock proteins, as well as, useful fragments thereof.

According to certain embodiments of the present invention, cells become cold-resistant by increasing the amount of proteins which are capable of reducing the detrimental effects of low temperatures which lead to reduced cell growth and cell death. For example, according to one aspect of the invention, cells are exposed to temperatures which sustain and promote normal growth referred to herein as "growth temperatures", i.e. 37° C., and are then exposed to lower temperatures where the cells remain viable but also where the production of cold-shock proteins is induced, e.g. 16° C. The cells are then preadapted by maintaining them at the lower temperature for a period of time sufficient to raise the cellular content of the cold-shock proteins to levels sufficient to enhance viability of the cells at still lower temperatures at which cells, which have not been preadapted, would not remain viable over time, e.g. 4° C. According to an alternate embodiment, the cells are preadapted in a temperature independent manner by exposing them to a chemical agent capable of inducing the production of cold-shock proteins to levels sufficient to enhance viability of the cells at low temperatures at which cells, which have not been preadapted, would not remain viable over time, e.g. 4° C. Chemical agents within the scope of the invention include those which lower the rate of protein synthesis thereby imitating the effect of a temperature downshift. Levels of cold-shock proteins sufficient to enhance viability of cells at temperatures where they would normally not remain viable include levels of cold-shock proteins above that normally produced by the cells, as well as, 2-fold amounts, 3-fold amounts, etc., and up to 10-fold amounts and beyond, since it has been discovered that increasing the cellular content of cold-shock proteins improves the cold-resistant characteristics of the cells.

It is to be understood that one of ordinary skill in the art based upon the teachings presented herein will be able to identify a temperature at which a particular cell type remains viable but also which induces the expression of cold-shock proteins. For example, temperatures between those at which cells grow normally, i.e. growth temperatures, and at which they would not remain viable with time are useful within the scope of the present invention. It is also to be understood that one of ordinary skill in the art based upon the teachings presented herein will be able to identify a temperature at which a particular cell type would not remain viable with time.

According to an alternate embodiment of the present invention, Trigger Factor ("TF") is discovered to be a cold-shock protein and further that TF and more particularly, the protein fragment responsible for the peptidyl-proline isomerase activity of TF, are useful in methods of increasing or enhancing cell viability at low temperatures by making the cells cold-resistant. Additional alternate embodiments of the present invention include the use of other proteins having peptidyl-proline isomerase activity in amounts sufficient to increase the viability of cells at low temperatures.

According to embodiments of the present invention, a method is presented whereby cells are analyzed for their ability to maintain viability at low temperatures by ascertaining the degree to which TF is produced and the degree to which cell viability at low temperatures is promoted. This method is useful in screening cells which have desirable cold-resistant characteristics which may then be used in further methods involving the cells at low temperatures.

According to an alternate embodiment, a method is practiced whereby cells are altered in a manner to express cold-shock proteins, such as TF, or useful fragments thereof having peptidyl-proline isomerase activity or other proteins having peptidyl-proline isomerase activity in amounts above those normally found at growth temperatures and in amounts sufficient to increase the viability of the cells at low temperatures. Embodiments of the present invention are still further directed to methods of making cells cold resistant by including genes and portions thereof which are capable of expressing cold-shock proteins, such as TF, or useful fragments thereof, or proteins that have peptidyl-proline isomerase activity or to altering a cell in a manner to regulate the naturally occurring gene to produce TF in a manner which increases cell viability at low temperatures.

It is accordingly an object of the present invention to provide methods of making cells cold resistant and to increasing the viability of microorganisms and plants at temperatures which prohibit normal cell growth and which lead to cell death.

Other objects, features or advantages of the present invention will become apparent from the following description taken in conjunction with the accompanying drawings.

BRIEF DESCRIPTION OF THE DRAWINGS

In the course of the detailed description of certain preferred embodiments to follow, reference will be made to the attached drawings, in which, FIG. 1 (SEQ ID NO: 1) shows the amino acid sequence of *E. coli* TF and a nucleotide sequence encoding *E. coli* TF.

FIG. 2A is a Western blot analysis showing the relative amounts of TF and GroEL in C600 cells grown in LB medium at different temperatures.

FIG. 2B is a Western blot analysis showing an increase in the amount of TF at 4° C. as compared with the production of TF at 37° C.

FIG. 3A is a graph showing rate of TF synthesis versus temperature shift.

FIG. 3B is a graph showing rate of TF synthesis before and after chloramphenicol addition.

FIG. 8 is a schematic of the Trigger Factor fragments with respective cloning vectors.

DETAILED DESCRIPTION OF CERTAIN PREFERRED EMBODIMENTS

Figure 5:
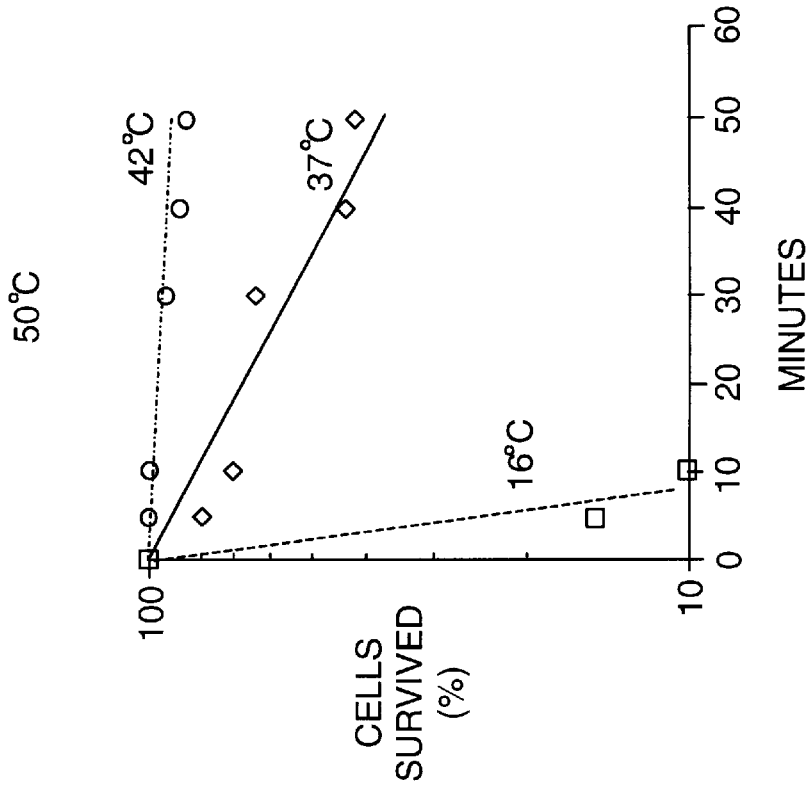
FIG. 5 is a graph showing percent survival over time at 50° C. of E. coli colonies conditioned at 16° C., 37° C. and 42° C.

In accordance with the teachings of the present invention, a method is provided through the use of cold-shock proteins to increase the cold resistance properties of cells at low temperatures that prevent normal cell growth and eventually lead to cell death. A protein produced at normal physiological temperatures known as Trigger Factor ("TF") has been discovered to act as a cold-shock protein, i.e. one whose production may be induced and, in fact increased, at low temperatures that prevent normal cell growth and lead to cell death. TF and fragments thereof having peptidyl-proline isomerase activity have also been discovered to increase cell viability at low temperatures when present in amounts above normally produced levels.

According to a first aspect of the present invention, TF is discovered to be expressed by cells in increasing amounts at temperatures of 16° C. and below, which demonstrates that the gene expressing TF is cold-shock inducible. Also, TF content has been discovered to increase at 4° C. where overall protein synthesis is extremely slow. According to this aspect of the invention, a method is provided whereby cells are exposed to growth temperatures and are then exposed to lower temperatures capable of inducing the production of cold-shock proteins and at which the cells remain viable. The cells are maintained at the lower temperatures for a period of time sufficient to raise their cellular content of cold-shock proteins to levels sufficient to enhance viability of the cells at temperatures where rapid cell growth is prevented and where cell death occurs. Alternatively, the cells are maintained at growth temperatures and are exposed to a chemical agent capable of inducing the production of cold-shock proteins. This method of preadapting cells to increase their cellular content of cold-shock proteins prior to subjecting them to low temperatures is particularly advantageous where it is desirable to maintain cells at refrigeration temperatures for a period of time that would normally lead to cell death. Preadapting or conditioning cells according to the method of the present invention will improve cell viability at the refrigeration temperature.

In accordance with an alternate embodiment of the present invention, E. coli bacteria were genetically altered to improve resistance to low temperatures and to increase cell viability. The E. coli cells were genetically altered in a manner to overexpress TF or fragments thereof having peptidyl-proline isomerase activity in amounts sufficient to increase the viability of the cells at low temperatures. The E. coli cells were also genetically altered to overexpress another cold-shock protein, Hsc66 to improve resistance to low temperatures. It is to be understood that the methods of the present invention are not limited to the specific cold-shock proteins TF or Hsc66, but rather, the invention encompasses other cold-shock proteins which are identified in the literature or suitable mutants or fragments thereof. While not wishing to be bound by any scientific theory, it is believed that the cold-shock proteins, in general, may be active in reducing the detrimental effects of low temperature on cells which lead to cell death, such as slowed protein metabolism, decreased ability to fold or refold proteins, decreased solubility, protein denaturation, decreased translation and the like which lead to cell death. Cold-shock proteins which reduce or eliminate the detrimental effects of low temperatures thereby increasing cell viability at low temperatures are useful in the present invention. Cold-shock proteins include csp A, csp B, csp C, NusA, B46.5, dihydrolipoamide acetyltransferase subunit of pyruvate dehydrogenase, RecA, polynucleotide phosphorylase, pyruvate dehydrogenase, H-NS, F10.6, F84.0, G74.0, G41.2, G55.0. See, for example, Jones, P. G., VanBogelen, R. A., and Neidhardt, F. C. (1987) *Journal of Bacteriology* 169(5), 2092–2095; and Jones, P. G., Cashel, M., Glaser, G., and Neidhardt, F. C. (1992) *Journal of Bacteriology* 174(12), 3903–3914.

It is also to be understood that the methods of the present invention are not limited to prokaryotic cells, since eukaryotic cells can also be altered by transfection to produce cold-shock proteins, such as bacterial TF or active fragments thereof in amounts sufficient to increase cell viability at low temperatures according to standard genetic methods well known in the art. It is also to be understood that other proteins having peptidyl-proline isomerase activity are useful within the scope of the present invention since it has been discovered that proteins having this activity enhance cell viability when over-expressed in cells at low temperatures. Many proline isomerase genes are known in plants and animals and they catalyze the interconversion of the cis and tyrans isomers of the peptidyl-prolyl (Xaa-Pro) bonds in peptide and protein substrates. Such peptidyl-proline isomerases include the families of compounds known as cyclophilins (CsA-binding proteins), FKBP (FK506/rapamycin-binding proteins), and parvulins (such as the E. coli PPIase, PpiC). Specific examples of peptidyl-proline isomerases are provided by Galat, A., *Eur. J. Biochem.*, 216, 689–707, and Rudd et al., *TIBS* (1995) 20, 12–14, each hereby incorporated by reference in its entirety.

The methods of the present invention include altering a cell to include promoters and/or genes which can be induced by cold-shock conditions or at low temperatures to overexpress cold-shock proteins, such as TF, or useful fragments thereof, or other proteins having peptidyl-proline isomerase activity, for example, where cold resistance is a desired trait of an agricultural product such as commercially valuable fruit or vegetable bearing plants. The methods further include altering a cell to continually over-express a cold-shock protein such as TF or a useful fragment thereof, or other proteins having peptidyl-proline isomerase activity, at normal growth temperatures or upon exposure to low temperatures where, for example, it is beneficial and useful for a cell to maintain viability for prolonged periods (e.g. upon cold-storage) or for a cell-based expression system to operate at low temperatures to produce certain proteins.

When over-expressed by a cell, certain cold-shock proteins such as TF, Hsp66 or useful fragments thereof, or peptides having peptidyl-proline isomerase activity have been discovered to contribute to or to induce cold tolerance or cold resistance to the cell. While not wishing to be bound by any scientific theory explaining these results, TF is believed to play a significant and valuable role in protecting cells from the detrimental effects of low temperatures, i.e. temperatures which are normally damaging or lethal to the cell, by promoting protein synthesis which would not ordinarily occur. The term "cold-tolerance" or "cold-resistance" as used herein means the property of the cells to remain viable to a greater extent at low temperatures at which they would not normally remain viable. The term "viable" does not necessarily mean the growing or multiplying of cells, but also includes a decrease or lowering in the death rate of the cells or an arrested condition where protein synthesis may be ongoing even though the growth of the cells or cell division is at a minimum or reduced rate. In this connection, "viable" also means that protein synthesis may still proceed in an organism transformed in accordance with the invention even though cell division and/or growth may be slowed down or arrested. As demonstrated herein, a method is provided whereby cells are altered to resist the detrimental effects of low temperature and to remain more viable when compared with cells which have not been so altered.

The invention uses principles and methodologies of recombinant DNA technology. Periodically herein, reference will be made to certain known principles, strategies or practices to assist the reader of this description.

The amino acid sequence of TF and the nucleotide sequence encoding TF have been described in Guthrie, B., and Wickner, W. (1990) *Journal of Bacteriology* 172(10), 5555 and are illustrated in FIG. 1. (SEQ ID NO: 1) However, it is to be understood that embodiments of the present invention are not limited to the particular amino acid sequence of TF, but also include useful fragments of TF and other peptides or proteins which are functionally or physiologically equivalent to TF's ability to increase the viability of cells at low temperatures. One such example of a functional or physiological equivalent of TF are segments or fragments of TF which retain the functional or physiological properties of the full length amino acid sequence of TF in increasing the viability of cells at low temperatures and include the fragment of TF having peptidyl-proline isomerase activity. Other examples of functional or physiological equivalents are other proteins or peptides having peptidyl-proline isomerase activity to the extent they increase the viability of cells at low temperatures. Also included within the scope of the invention are other cold-shock proteins which are effective in reducing the detrimental effects of low temperatures on cells and promote cell viability at low temperatures.

Likewise, it is to be understood that the invention is not limited to the particular nucleotide sequence described in FIG. 1. (SEQ ID NO: 1) As is known, the genetic code is degenerate in the sense that different codons may yield the same amino acid, but precise in that for each amino acid, there any only one or more codons for it and no other. Thus the invention includes within its scope those nucleotide sequences in which any one or several codons are replaced by any one or more codons capable of encoding the same amino acid. Thus, functionally equivalent sequences are within the scope of the invention whose translation brings about TF, or fragments of TF having peptidyl-proline isomerase activity or other peptides or proteins having peptidyl-proline isomerase activity. The term "functionally" used herein means the functional equivalent of a DNA sequence with the gene (or fraction thereof) which encodes TF (or a functional portion thereof) or a protein which confers or contributes to conferring cold-tolerance to the transformed organism, or in general, for the organism to develop under conditions which normally do not support cell growth and viability. The term "physiologically" equivalent means herein a protein or polypeptide which has physiological or biological function at low temperatures that is equivalent to that of TF or fragments thereof having peptidyl-proline isomerase activity which can be expressed by organisms to increase the viability of cells at low temperatures. It is to be understood that once a particular cold-shock protein or mutant or useful fragment thereof has been identified, its corresponding nucleic acid sequence encoding the cold-shock protein can then be determined by one of ordinary skill in the art based upon the genetic code.

Embodiments of the present invention include methods comprising eukaryotic or prokaryotic organisms that when subjected to cold-shock conditions or chemical agents, are able to generate cold-shock proteins, such as TF to increase the cold-resistance characteristic of the cell. In a preferred embodiment, the nucleotide sequence which encodes a cold-shock protein, such as TF (or a useful fragment thereof) is induced and then over-expressed by the organism, whether the cell has been altered to include the nucleotide sequence or altered in a manner to over-express the naturally occurring nucleotide sequence. Such methods are useful whether the cell is induced under cold shock conditions or by a chemical agent to express the cold-shock protein or whether the cell has been altered to continually express the cold-shock protein, such as TF, in an amount sufficient to increase cold resistance and/or cell viability at low temperatures.

Among eukaryotes which are of particular interest are eukaryotic microorganisms (e.g. yeast), plant or vegetable cells, cells of insects, and mammalian cells to be subjected to low temperature shock in accordance with the invention. The cells of the organisms described above can be grown as described in the literature generally at about 37° C. and then subjected to cold-shock conditions to any lower temperature like 20° C., 16° C., 15° C., 10° C., 7° C., 5° C., 4° C., 0° C. preparations and methodology described herein, the amount of cold-shock protein, such as TF, produced in response to the cold-shock can be ascertained and the cell characterized for its low temperature tolerance based on that amount. Cells having a higher cellular content of the cold-shock protein are characterized as being better able to resist the detrimental effects of low temperatures, i.e. they have better cold-resistance characteristics.

Specifically, plant cells can be cultured and tested for induction by cold-shock of TF production and the ability to confer low temperature tolerance. Cell culturing techniques are known. Plants of particular interest include agricultural crops like corn, wheat, rye, barley, rice, tobacco, coffee, tea, and numerous others. Genetic engineering methods are described in Genome Organization and Expression in Plants, Ed. Leaver, Plenum Press (1980) and to Genetic Engineering of Plants, Ed. Kosuge et al., Plenum Press (1982).

The induction of cold shock genes in plants and their transformation is of particular interest in that one is able to confer to the transformed plants the desirable characteristic of low temperature tolerance. This has, of course, major benefits in allowing the plants to grow over a wider or different climatic area and be more tolerant of temperature extremes.

Embodiments of the present invention find advantage in cell-based expression systems. Numerous valuable proteins are synthesized today by transformed microorganisms (eukaryotes and prokaryotes). Of particular interest are eukaryotes such as yeasts and prokaryotes such as bacteria. A convenient source of suitable yeasts is found in the ATCC Catalogue of Yeasts, 18th Ed. 1990. Likewise, useful prokaryotic bacterial strains are publicly available and listed in ATCC Catalogue of Bacteria and Bacteriophages, 17th Edition, 1989.

Strains over-expressing cold-shock proteins, such as TF, useful fragments thereof or other proteins having peptidyl-proline isomerase activity are also envisioned to be capable of over-expressing target proteins at low temperatures. The microorganisms can be transformed with appropriate multi-cloning vectors or other appropriate vectors. Additionally, the microorganism may be transformed with an endogenous promoter element for a cold-shock protein, such as TF, fragments of TF having peptidyl-proline isomerase activity or other non-TF proteins having peptidyl-proline isomerase activity and a selected DNA sequence encoding a desired physiologically active protein. Typical of physiologically active proteins include hGH, somatostatin, FSH, hCG, t-PA, insulin, interferon (alpha, beta, etc.), erythropoietin, and many others. An advantage of the method of the present invention is that the host cells transformed in a manner to express the cold-shock protein such as TF, fragments of TF having peptidyl-proline isomerase activity or other non-TF proteins having peptidyl-proline isomerase activity in amounts sufficient to increase cell viability at low temperatures can express the physiologically active proteins with less risks of decrease activity than if grown and/or expressed at conventional temperatures. Moreover, these overproduced cold-shock proteins, such as TF or Hsc66, appear to promote protein folding or to prevent aggregation at low temperatures in particular.

The following examples are set forth as representative of the present invention. These examples are not to be construed as limiting the scope of the invention as these and other equivalent embodiments will be apparent in view of the present disclosure, figures, and accompanying claims.

EXAMPLE I

Trigger Factor Content Increases At Low Temperatures

The following example was used to demonstrate that TF content increases at low temperatures where the growth of cells is reduced. The wild type C600 strain of *E. coli.* was grown to mid-log phase in LB medium at temperatures ranging from 16° C. to 42° C. When the cells reached the same optical density ($A_{600}$0.5), equal aliquots were taken, and cells collected by centrifugation. Cell proteins were analyzed by SDS PAGE, and the amounts of TF were measured by Western blot with an anti-TF antibody and $^{125}$I-protein A. For comparison, the levels of the heat shock protein, GroEL were measured by a similar approach using an anti-GroEL antibody. As indicated in FIG. 2A, at 42° C., when GroEL content reached its maximum, TF content was lowest. By contrast, at 16° C., TF content was 2–3 fold higher than in the culture growing at 37° C., even though GroEL content fell significantly in cultures grown below 27° C. Furthermore as indicated in FIG. 2B, when cells growing logarithmically at 37° C. were transferred to 4° C. for 48 hours, TF content also increased about 2-fold. Thus, although GroEL and TF can function together, TF's functions are not limited to those connected to GroEL since their expression is regulated in opposite fashions, and the production of TF increases at low temperatures.

EXAMPLE II

Trigger Factor Synthesis Is Induced At Low Temperatures

*E. coli.* cultures (C600 cells) were initially grown in Davis minimal medium supplemented with amino acids and glucose at 37° C. until mid-log phase and then temperature shifted to 10° C. where it was observed that culture growth ceased for about 4 hours and then reinitiated exponential growth, but at a lower rate, in accord with prior observations. See Ng, H., Ingraham, J. L., and Marr, A. G. (1962) *Journal of Bacteriology* 84, 331–339. To label cell proteins, 1 ml aliquotes were taken at different times and incubated with $^{35}$S methionine (10 $\mu$Ci/ml) for 5 min at 37° C. (sample 1) and for 60 min at the following times after the shift to 10° C.: 0 to 60 min (sample 2), 60 to 120 min (sample 3), 120 to 180 min (sample 4) and 180 to 240 min (sample 5). Cells were collected by centrifugation, and proteins solubilized by boiling in a buffer containing 0.3% SDS. After a 50-fold dilution with the immunoprecipitation buffer to reduce the SDS concentration, equivalent amounts of radioactive cell proteins were analyzed by immunoprecipitation with a specific anti-TF antibody and protein A-Trisacryl followed by SDS PAGE and autoradiography, the results of which are presented in FIG. 3A. Rates of incorporation of $^{35}$S methionine into TF were measured before and after the shift to 10° C. During the first two hours at 10° C. (samples 2 and 3), the differential rate of TF synthesis decreased (i.e. the rate as a fraction of total protein synthesis), but then it increased markedly and during the third and fourth hours (samples 4 and 5), TF synthesis was at least 2-fold higher than at 37° C. With the subsequent resumption of growth at 10° C., the differential rate of TF synthesis remained slightly higher than at 37° C. A similar sequence of changes in TF synthesis was found upon shift of the cells from 37° C. to 16° C. This pattern of changes in TF synthesis resembles exactly the pattern characteristic of cold-shock proteins in general as described in Jones et al., (1987) *Journal of Bacteriology* 169(5) 2092–2095.

EXAMPLE III

Trigger Factor is Synthesized in a Manner Similar to Other Cold Shock Proteins

Previous studies have shown that cold shock proteins can be induced at 37° C. by a specific group of antibiotics that reduce the rate of translation, including chloramphenicol, tetracycline, erythromycin, spiramycin, and fusidic acid. See VanBogelen, R. A., and Neidhardt, F. C. (1990) *Proceedings of the National Academy of Sciences* 87(15) 5589–5593. TF synthesis was shown to also be stimulated under these conditions in the following manner. Wild type *E. coli* (C600 cells) were grown in Davis minimal medium supplemented with amino acids and glucose at 37° C. to mid-log phase and chloramphenicol added at a final concentration of 20 $\mu$g/ml which reduced but did not prevent cell growth. Cell proteins were labeled for 5 min with $^{35}$S methionine (10 $\mu$Ci/ml) just before and 30 min after chloramphenicol addition. The amount of radiolabeled TF was determined as described in Example II above.

As shown in FIG. 3B, the differential rate of TF synthesis increased approximately 2-fold by 30 minutes after chloramphenicol treatment. By contrast, differential rate of synthesis of GroEL was reduced in the presence of chloramphenicol (data not shown), in accord with prior findings. Thus, synthesis of TF was demonstrated to be regulated in a similar way as synthesis of other cold-shock proteins and in an opposite fashion to the heat shock proteins.

EXAMPLE IV

Cells Preadapted to Temperatures Which Induce Cold-Shock Protein Production Show Enhanced Viability at Low Temperatures E. coli cultures (C600 cells) were initially grown in Davis minimal medium supplemented with amino acids and glucose at 37° C. until mid-log phase. Equal amounts of E. coli cells were then plated onto three sets of Petri dishes. The first set was maintained at 37° C., the second set was incubated at 16° C. for four hours to induce cold-shock protein production, and the third set was incubated at 42° C. for 0.5 hours to induce heat shock. Alternatively, the second set may be exposed to inhibitors of protein synthesis such as chloramphenicol or other antibiotics as in Example III to induce cold-shock protein production. After these incubations, aliquots containing equal amounts of cells were then taken from each culture and plated onto three separate sets of Petri dishes which were then further incubated at 40° C. In addition, aliquots containing equal amounts of cells were also taken from each culture and plated onto three separate sets of Petri dishes which were then further incubated at 50° C. At different times, sets of plates were transferred to 37° C. and the surviving colonies were counted.

Figure 4:
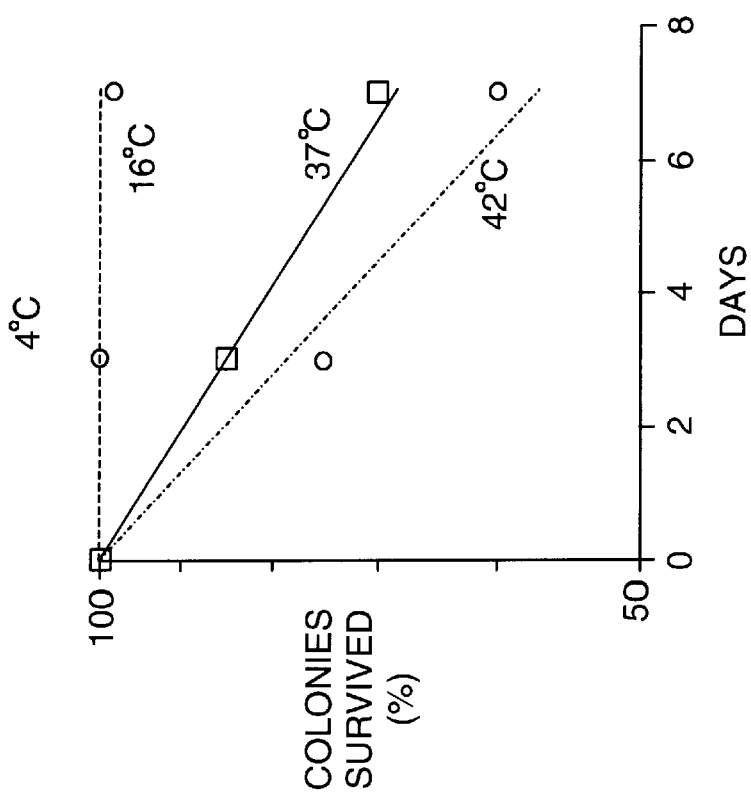
FIG. 4 is a graph showing percent survival over time at 4° C. of E. coli colonies conditioned at 16° C., 37° C. and 42° C.

As shown in FIG. 4 which is a plot of the percentage of colonies surviving over time at 4° C., the sets of cultures preadapted to 37° C. and 42° C. lost viability exponentially over a period of eight days after being temperature shifted to 4° C., however, the set of cells preadapted at 16° C. to induce cold-shock proteins remained almost completely viable after temperature shift to 4° C. with little cell death occurring over the same eight day period. FIG. 4 demonstrates the advantageous cold-tolerance effect of induced cold-shock proteins, which is particularly useful to improve the viability of cells which are to be later exposed to temperatures where the cell would not normally remain viable.

As shown in FIG. 5 which is a plot of percentage of colonies surviving over time at 50° C., the culture conditioned at 16° C. to induce cold-shock proteins lost viability very rapidly in less than 10 minutes while the culture conditioned at 37° C. lost viability but at a much slower rate. The culture conditioned at 42° C. to induce heat shock proteins remained extremely viable after temperature shift to 50° C. with little cell death occurring after approximately one hour. FIG. 5 demonstrates that increased cold-shock proteins, in general, reduce viability of cells at high temperatures.

EXAMPLE V

Increased Trigger Factor Content Enhances Cell Viability at Low Temperatures

E. coli. strains genetically modified as described in Guthrie, B., and Wickner, W. (1990) Journal of Bacteriology 172(10), 5555–5562 to express TF at either very high or very low levels were used to determine whether TF content had any effect on cell viability at temperatures where rapid cell growth is prevented and at which cell death normally occurs over time. In accordance with standard genetic engineering methods, the TF-over-expressing strain was modified to include the tig gene on a multicopy plasmid (pTIG2) under the regulation of the arabinose promotor. Therefore, in the presence of arabinose, the content of TF was demonstrated to increase more than 10-fold. Cells expressing low levels of TF had the tig gene integrated into the chromosome under the control of the ara promotor. Therefore, when grown in medium containing glucose instead of arabinose, TF synthesis was demonstrated to be repressed, and its level fell by over 90%. When these strains were grown in the presence of arabinose or glucose at 20° C., 30° C., 37° C., or 42° C., they grew at similar rates as wild type cells in the same media and at the same temperature.

Wild type, TF-overproducing, and TF-underproducing strains were grown until mid-log phase at 37° C. in LB medium supplemented with arabinose to induce TF overexpression or glucose to inhibit TF expression. Equal amounts of the TF-overproducing or TF-underproducing cells from each culture were then plated on Petri dishes containing arabinose or glucose, respectively and incubated at 4° C. At different times, the number of colonies surviving at 4° C. were measured by transferring the plates to 37° C.

Figure 6B:
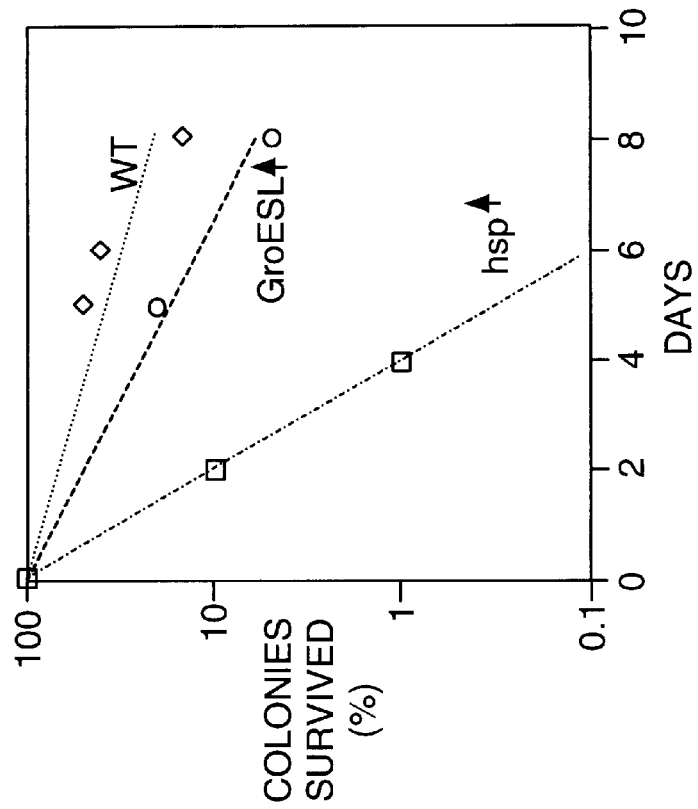
FIG. 6B is a graph showing percent survival over time at 4° C. of E. coli colonies modified to increase heat shock proteins in general, and to increase production of GroEL/ES compared to wild-type E. coli.
Figure 6A:
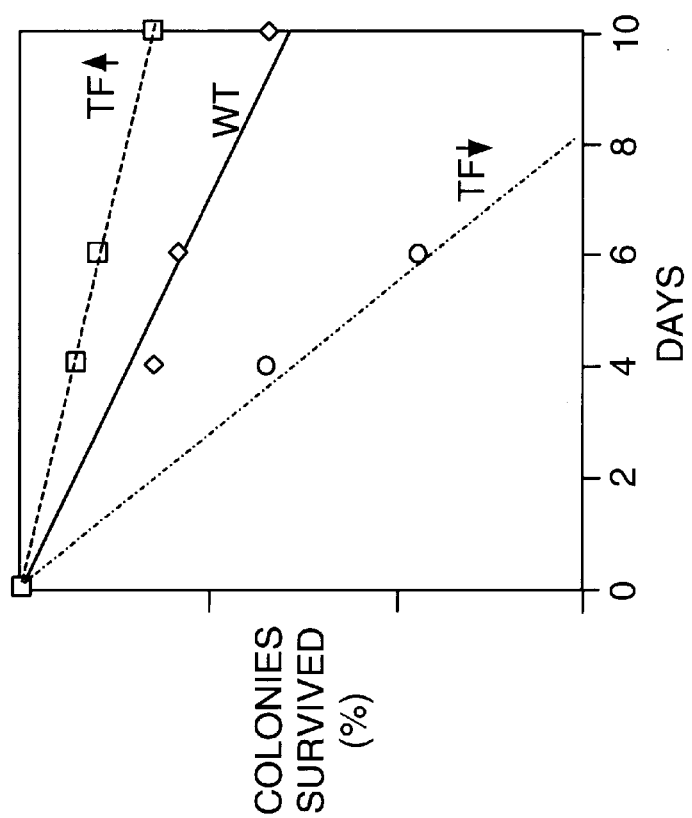
FIG. 6A is a graph showing percent survival over time at 4° C. of E. coli colonies modified to increase and decrease TF production as compared to wild type E. coli.

As shown in FIG. 6A, all three cultures lost viability exponentially, but at quite different rates. The wild type cells died with a half-life of 4–5 days whether they were grown in arabinose- or glucose-containing media. After a week at 4° C., 15% of the cells remained alive. By contrast, only 1% of the TF-underproducing cells survived after a week, while 40% of the TF-overproducing cells were still viable at this time ($t_{1/2}$=6–7 days).

In separate experiments, E. coli strains were genetically modified as previously described to express TF from between 3- to 10-fold of the amount of TF produced at room temperature. As demonstrated above, TF content of wild-type cells can be increased up to 2-fold upon shift from 37° C. to either 10° C. or 16° C. for several hours. Experiments were then conducted to determine the degree of protection afforded by these various TF levels between 3- to 10-fold. The degree of protection was found to be comparable to that where the content of TF was increased up to 10-fold. Thus, decreased TF content markedly reduced cell viability in the cold, while increased TF levels, even on the order of a 2–3 fold increase, enhanced the cold resistance of the E. coli cells at low temperatures.

EXAMPLE VI

Increased Heat Shock Proteins In General or GroES/EL Reduce Cell Viability at Low Temperatures The induction of TF and its ability to protect cells at low temperatures appear analogous to the properties of the various heat shock proteins, which are induced as temperature rises and protect cells against high temperatures. "Heat-shock" proteins are generally referred to as "stress proteins" because of their ability to protect cells against a variety of harsh conditions, e.g. exposure to solvents or oxygen radicals. Similar experiments were conducted to determine whether cells carrying high levels of heat-shock proteins (hsps) generally or just high levels of GroEL and GroES are protected against loss of viability at 4° C., as in the case of TF. To increase the production and cellular content of heat shock proteins, wild type cells carrying the pUHE211-1 plasmid containing the heat shock protein specific subunit of RNA polymerase σ-factor, σ32, or the GroEL/ES operon on a plasmid under the control of the lac promotor were grown to mid-log phase in LB at 37° C. Each culture was then divided into two parts. IPTG (1 mM) was added to one of the parts, and the cultures then continued growing for two more hours. The effect of overproduction of heat shock proteins or GroES/EL on cell viability at low temperatures was determined as in Example V.

As indicated in FIG. 6B, cells grown at 37° C. in the presence of IPTG and then shifted to 4° C. actually lost viability and were killed much faster than wild-type cells. The cells over-expressing all heat-shock proteins lost viability with a half-life of about 1 day, and those over-expressing GroES/EL with a half-life of 3 days, compared to 5 days for wild type. The induction of heat-shock proteins is deleterious to cells at low temperatures and promotes loss of viability at 4° C. Cold-shock proteins, therefore, operate to protect cells at low temperatures in a manner different from the mechanism by which stress proteins protect cells.

EXAMPLE VII

Increased Hsc66 Content Enhances Cell Viability at Low Temperatures

E. coli. strains genetically modified as described in Example V to express Hsc66, a cold-shock protein that is a member of the hsp 70 family of chaperones and thus a homolog of the E. coli heat shock protein Dna K, at increased levels were used to determine whether Hsc66 content had any effect on cell viability at low temperatures according to the method of Example V.

Figure 7:
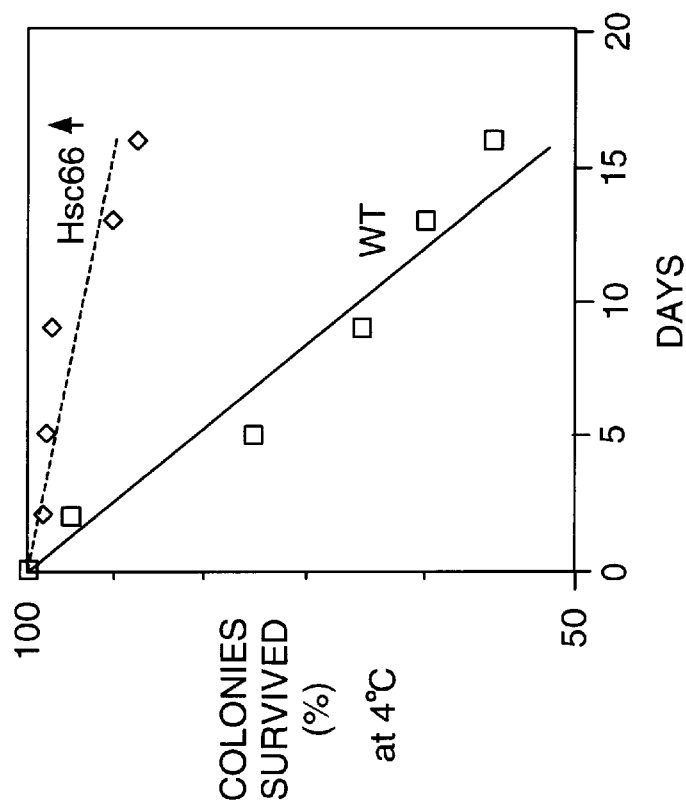
FIG. 7 is a graph showing percent survival over time at 4° C. of E. coli colonies modified to increase Hsc66 compared to wild-type E. coli.

As shown in FIG. 7, the wild-type cells at 4° C. lost viability exponentially with a half-life of about 15 days while the Hsc66 overproducing culture remained approximately 90% viable at 4° C. over the same time period confirming that the overproduction of cold-shock proteins in cells at low temperatures makes the cells cold-resistant and enhances cell viability.

In addition, in a separate experiment, a mutant defective in the major cold-shock protein csp A, also appeared protective against low temperatures, although less than TF or Hsc 66.

EXAMPLE VIII

Increased Content of the Proline Isomerase Domain of Trigger Factor Enhances Cell Viability at Low Temperatures The effects of fragments of TF were studied to determine whether TF's PPI activity has any effect on TF's ability to enhance cell viability at low temperatures. Four fragments of TF were used in the following study: the amino-terminal fragment (N) including residues 1–145 (where residue 1 corresponds to the amino acid encoded by nucleic acids 181, 182 and 183 beginning at the arrow as shown in FIG. 1) (SEQ ID NO: 1), the middle domain 12 kDa fragment (M or PPIase) including residues 145–251, a combination of the N and M domains (NM) and the carboxy-terminal fragment (C) including residues 251–432. PPIase assays of the purified fragments were conducted by measuring cleavage of the tetrapeptide Suc-AFPF-p-NA by chymotrypsin. Assay results confirmed that the amino-terminal fragment and the carboxy-terminal fragment lacked PPI activity and that the PPI activity of TF was localized to the middle domain fragment. TF-overproducing E. coli strains were prepared as previously described. Fragment-overproducing strains were provided where the N, M and C fragments were overexpressed under the regulation of a lac promoter. Fusion proteins containing fragments of the TF protein are shown in FIG. 8.

Wild type (E. coli C600), TF-overproducing and fragment-overproducing (PPIase, NM, N and C) strains were grown until mid-log phase at 37° C., induced with IPTG for 30 minutes and then plated. Petri dishes were then incubated at 4° C. for varying times. Surviving colonies were counted after incubation at 37 ° C. overnight. The results are shown in Table 1 below.

TABLE 1

C600 Cells Overexpressing Whole TF or a Fragment Thereof on a Plasmid Compared with Unaltered Wild-Type C600 Cells

| Days | Wild-Type C600 Cells | Whole TF | M | NM | N | C |
|---|---|---|---|---|---|---|
| 0 | 100 | 100 | 100 | 100 | 100 | 100 |
| 4 | 37.5 | 80 | 81.8 | 80 | 37 | 60 |
| 6 | 8.5 | 30 | 30.9 | 51 | 1.8 | 3 |
| 7 | 2.5 | 0 | 10 | 14 | 1.2 | 0 |

As shown in Table 1, after 6 days, less than 10% of the wild-type cells E. coli survived, while over 30% of cells overproducing the PPIase domain of TF (M) remained alive. A strain overproducing a TF fragment containing both the amino-terminal and PPIase domains of TF (NM, residues 1–251) showed better cold survival than wild-type cells. Cells overproducing the TF amino-terminal fragment (N) or the TF carboxy-terminal fragment (C) showed survival rates similar or lower when compared to the wild-type and lacked the low temperature protective effect of the middle domain fragment (M).

EXAMPLE IX

Increased Trigger Factor Content Reduces Cell Viability at High Temperatures

Figure 9:
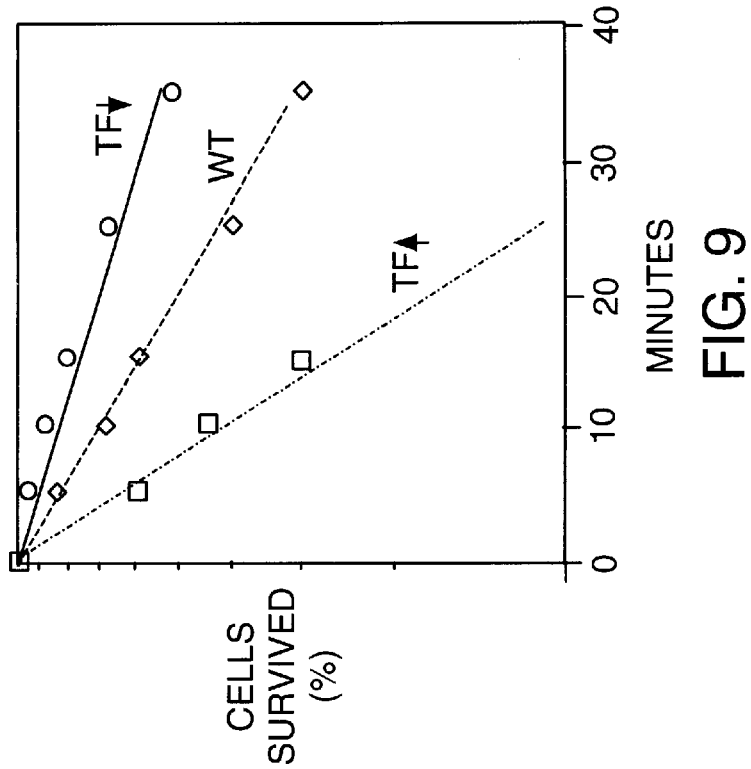
FIG. 9 is a graph showing percent survival over time at 50° C. of E. coli colonies modified to increase TF production and to decrease TF production compared to wild-type E. coli.

To determine the effect of increased TF content on cell viability at elevated temperatures, TF-overexpressing and TF-underexpressing cultures were prepared as described above. These cultures were grown along with wild-type strains to mid-log phase and then shifted to 50° C., where E. coli die rapidly. Aliquots were then taken from each culture at 5 minute intervals and plated on Petri dishes at 37° C. to determine the number of cells remaining viable. As can be seen in FIG. 9, at 50° C., wild-type cells lost viability with a half-life of 20 minutes. In contrast to the protection observed at 4° C., at 50° C., the cells containing high amounts of TF died much faster (half-life of 7 minutes) while those with reduced TF levels survived longer (half-life of 35 minutes) than did the wild-type cells. This result suggests that the induction of TF at high temperatures has the opposite effect on cellular survival as heat-shock proteins and that it would be advantageous for a cell to reduce its TF content at elevated temperatures above 37° C., which has been observed as shown in FIG. 2A.

It is to be understood that the embodiments of the invention which have been described are merely illustrative of some applications of the principles of the present invention. Numerous modification may be made by those skilled in the art without departing from the true spirit and scope of the invention.

0

We claim:

1. A method of improving viability of a cell at low temperatures comprising exposing a cell to a first temperature where the cell remains viable; inducing the cell at the first temperature to produce a cold-shock protein, wherein the cold-shock protein is Trigger Factor; maintaining the cell at the first temperature for a period of time sufficient to increase the cellular content of the cold-shock protein to an amount sufficient to increase the viability of the cell at a second temperature at which the cell's viability decreases; and exposing the cell to the second temperature.

2. A method of improving viability of a cell at low temperatures comprising altering a cell to express a cold-shock protein, wherein the cold-shock protein is Trigger Factor, in an amount above that normally produced by the cell in an unaltered state at room temperature; producing the cold-shock protein in the cell in an amount to increase viability of the cell at a low temperature at which the cell's viability decreases when in the unaltered state; and exposing the cell to the low temperature.

3. A method of improving viability of a cell at low temperatures comprising altering a cell to express a cold-shock protein, wherein the cold-shock protein is a fragment of Trigger Factor having peptidyl-proline isomerase activity, in an amount above that normally produced by the cell in an unaltered state at room temperature; producing the cold-shock protein in the cell in an amount to increase viability of the cell at a low temperature at which the cell's viability decreases when in the unaltered state; and exposing the cell to the low temperature.

4. The method of claim 3 wherein the fragment of Trigger Factor comprises amino acids 145–251 of Trigger Factor.

* * * * *

SEQUENCE LISTING

<160> NUMBER OF SEQ ID NOS: 4

<210> SEQ ID NO 1
<211> LENGTH: 1809
<212> TYPE: DNA
<213> ORGANISM: Escherichia coli
<220> FEATURE:
<221> NAME/KEY: CDS
<222> LOCATION: (181)..(1809)

<400> SEQUENCE: 1

```
cgttctcgac tcataaaagt gatgccgcta taatgccgcg tcctatttga atgctttcgg      60
gatgattctg gtaacaggga atgtgattga ttataagaac atcccggttc cggcgaagcc     120
aacaacctgt gcttgcgggg taagagttga ccgagcactg tgattttttg aggtaacaag    180
```

```
atg caa gtt tca gtt gaa acc act caa ggc ctt ggc cgc cgt gta acg     228
Met Gln Val Ser Val Glu Thr Thr Gln Gly Leu Gly Arg Arg Val Thr
  1               5                  10                  15 att act atc gct gct gac agc atc gag acc gct gtt aaa agc gag ctg     276
Ile Thr Ile Ala Ala Asp Ser Ile Glu Thr Ala Val Lys Ser Glu Leu
             20                  25                  30 gtc aac gtt gcg aaa aaa gta cgt att gac ggc ttc cgc aaa ggc aaa     324
Val Asn Val Ala Lys Lys Val Arg Ile Asp Gly Phe Arg Lys Gly Lys
         35                  40                  45 gtg cca atg aat atc gtt gct cag cgt tat ggc gcg tct gta cgc cag     372
Val Pro Met Asn Ile Val Ala Gln Arg Tyr Gly Ala Ser Val Arg Gln
     50                  55                  60 gac gtt ctg ggt gac ctg atg agc cgt aac ttc att gac gcc atc att     420
Asp Val Leu Gly Asp Leu Met Ser Arg Asn Phe Ile Asp Ala Ile Ile
 65                  70                  75                  80 aaa gaa aaa atc aat ccg gct ggc gca ccg act tat gtt ccg ggc gaa     468
Lys Glu Lys Ile Asn Pro Ala Gly Ala Pro Thr Tyr Val Pro Gly Glu
                 85                  90                  95 tac aag ctg ggt gaa gac ttc act tac tct gta gag ttt gaa gtt tat     516
Tyr Lys Leu Gly Glu Asp Phe Thr Tyr Ser Val Glu Phe Glu Val Tyr
            100                 105                 110 ccg gaa gtt gaa ctc gag ggt ctg gaa gcg atc gaa gtt gaa aaa ccg     564
Pro Glu Val Glu Leu Glu Gly Leu Glu Ala Ile Glu Val Glu Lys Pro
        115                 120                 125 atc gtt gaa gtg acc gac gct gac gtt gac ggc atg ctg gat act ctg     612
Ile Val Glu Val Thr Asp Ala Asp Val Asp Gly Met Leu Asp Thr Leu
    130                 135                 140 cgt aaa cag cag gcg acc tgg aaa gaa aaa gac ggc gct gtt gaa gca     660
Arg Lys Gln Gln Ala Thr Trp Lys Glu Lys Asp Gly Ala Val Glu Ala
145                 150                 155                 160 gaa gac cgc gta acc atc gac ttc acc ggt tct gta gac ggc gaa gag     708
Glu Asp Arg Val Thr Ile Asp Phe Thr Gly Ser Val Asp Gly Glu Glu
                165                 170                 175 ttc gaa ggc ggt aaa gcg tct gat ttc gta ctg gcg atg ggc cag ggt     756
Phe Glu Gly Gly Lys Ala Ser Asp Phe Val Leu Ala Met Gly Gln Gly
            180                 185                 190 cgt atg atc ccg ggc ttt gaa gac ggt atc aaa ggc cac aaa gct ggc     804
Arg Met Ile Pro Gly Phe Glu Asp Gly Ile Lys Gly His Lys Ala Gly
        195                 200                 205 gaa gag ttc acc atc gac gtg acc ttc ccg gaa gaa tac cac gca gaa     852
Glu Glu Phe Thr Ile Asp Val Thr Phe Pro Glu Glu Tyr His Ala Glu
    210                 215                 220 aac ctg aaa ggt aaa gca gcg aaa ttc gct atc aac ctg aag aaa gtt     900
Asn Leu Lys Gly Lys Ala Ala Lys Phe Ala Ile Asn Leu Lys Lys Val
```

```
                225                 230                 235                 240 gaa gag cgt gaa ctg ccg gaa ctg act gca gaa ttc atc aaa cgt ttc        948
Glu Glu Arg Glu Leu Pro Glu Leu Thr Ala Glu Phe Ile Lys Arg Phe
                    245                 250                 255 ggc gtt gaa gat ggt tcc gta gaa ggt ctg cgc gct gaa gtg cgt aaa        996
Gly Val Glu Asp Gly Ser Val Glu Gly Leu Arg Ala Glu Val Arg Lys
            260                 265                 270 aac atg gag cgc gag ctg aga gcg cca tcc gta acc gcg tta agt tct       1044
Asn Met Glu Arg Glu Leu Arg Ala Pro Ser Val Thr Ala Leu Ser Ser
        275                 280                 285 cag gcg atc gaa ggt ctg gta aaa gct aac gac atc gac gta ccg gct       1092
Gln Ala Ile Glu Gly Leu Val Lys Ala Asn Asp Ile Asp Val Pro Ala
    290                 295                 300 gcg ctg atc gac agc gaa atc gac gtt ctg cgt cgc cag gct gca cag       1140
Ala Leu Ile Asp Ser Glu Ile Asp Val Leu Arg Arg Gln Ala Ala Gln
305                 310                 315                 320 cgt ttc ggt ggc aac gaa aaa caa gct ctg gaa ctg ccg cgc gaa ctg       1188
Arg Phe Gly Gly Asn Glu Lys Gln Ala Leu Glu Leu Pro Arg Glu Leu
                325                 330                 335 ttc gaa gaa cag gct aaa cgc cgc gta gtt gtt ggc ctg ctg ctg ggc       1236
Phe Glu Glu Gln Ala Lys Arg Arg Val Val Val Gly Leu Leu Leu Gly
            340                 345                 350 gaa gtt atc cgc acc aac gag ctg aaa gct gac gaa gag cgc gtg aaa       1284
Glu Val Ile Arg Thr Asn Glu Leu Lys Ala Asp Glu Glu Arg Val Lys
        355                 360                 365 ggc ctg atc gaa gag atg gct tct gcg tac gaa gat ccg aaa gaa gtt       1332
Gly Leu Ile Glu Glu Met Ala Ser Ala Tyr Glu Asp Pro Lys Glu Val
    370                 375                 380 atc gag ttc tac agc aaa aac aaa gaa ctg atg gac aac atg cgc aat       1380
Ile Glu Phe Tyr Ser Lys Asn Lys Glu Leu Met Asp Asn Met Arg Asn
385                 390                 395                 400 gtt gct ctg gaa gaa cag gct gtt gaa gct gta ctg gcg aaa gcg aaa       1428
Val Ala Leu Glu Glu Gln Ala Val Glu Ala Val Leu Ala Lys Ala Lys
                405                 410                 415 gtg act gaa aaa gaa acc act ttc aac gag ctg atg aac cag cag gcg       1476
Val Thr Glu Lys Glu Thr Thr Phe Asn Glu Leu Met Asn Gln Gln Ala
            420                 425                 430 taa ttt acg cag cat aac gcg cta aat tcg cac aaa ggc ccg tca ccg       1524
    Phe Thr Gln His Asn Ala Leu Asn Ser His Lys Gly Pro Ser Pro
        435                 440                 445 cca ggt ggt ggg ctt ttt ttt gtc atg aat ttt gca tgg aac cgt gcg       1572
Pro Gly Gly Gly Leu Phe Phe Val Met Asn Phe Ala Trp Asn Arg Ala
    450                 455                 460 aaa agc ctc ttt cgg tgt tag cgt aac aac aaa aga ttg tta tgc ttg       1620
Lys Ser Leu Phe Arg Cys     Arg Asn Asn Lys Arg Leu Leu Cys Leu
465                 470                 475                 480 aaa tat ggt gat gcc gta ccc ata aca cag gga cta gct gat aat ccg       1668
Lys Tyr Gly Asp Ala Val Pro Ile Thr Gln Gly Leu Ala Asp Asn Pro
                485                 490                 495 tcc ata agg tta caa tcg gta cag cag gtt ttt tca att tta tcc agg       1716
Ser Ile Arg Leu Gln Ser Val Gln Gln Val Phe Ser Ile Leu Ser Arg
            500                 505                 510 aga cgg aaa tgt cat aca gcg gcg aac gag ata act ttg cac ccc ata       1764
Arg Arg Lys Cys His Thr Ala Ala Asn Glu Ile Thr Leu His Pro Ile
        515                 520                 525 tgg cgc tgg tgc cga tgg tca ttg aac aga cct cca cgc ggt gag            1809
Trp Arg Trp Cys Arg Trp Ser Leu Asn Arg Pro Pro Arg Gly Glu
    530                 535                 540
```

```
<210> SEQ ID NO 2
<211> LENGTH: 432
<212> TYPE: PRT
<213> ORGANISM: Escherichia coli

<400> SEQUENCE: 2

Met Gln Val Ser Val Glu Thr Thr Gln Gly Leu Gly Arg Arg Val Thr
 1               5                  10                  15

Ile Thr Ile Ala Ala Asp Ser Ile Glu Thr Ala Val Lys Ser Glu Leu
                20                  25                  30

Val Asn Val Ala Lys Lys Val Arg Ile Asp Gly Phe Arg Lys Gly Lys
            35                  40                  45

Val Pro Met Asn Ile Val Ala Gln Arg Tyr Gly Ala Ser Val Arg Gln
        50                  55                  60

Asp Val Leu Gly Asp Leu Met Ser Arg Asn Phe Ile Asp Ala Ile Ile
 65                  70                  75                  80

Lys Glu Lys Ile Asn Pro Ala Gly Ala Pro Thr Tyr Val Pro Gly Glu
                85                  90                  95

Tyr Lys Leu Gly Glu Asp Phe Thr Tyr Ser Val Glu Phe Glu Val Tyr
                100                 105                 110

Pro Glu Val Glu Leu Glu Gly Leu Glu Ala Ile Glu Val Glu Lys Pro
            115                 120                 125

Ile Val Glu Val Thr Asp Ala Asp Val Asp Gly Met Leu Asp Thr Leu
        130                 135                 140

Arg Lys Gln Gln Ala Thr Trp Lys Glu Lys Asp Gly Ala Val Glu Ala
145                 150                 155                 160

Glu Asp Arg Val Thr Ile Asp Phe Thr Gly Ser Val Asp Gly Glu Glu
                165                 170                 175

Phe Glu Gly Gly Lys Ala Ser Asp Phe Val Leu Ala Met Gly Gln Gly
                180                 185                 190

Arg Met Ile Pro Gly Phe Glu Asp Gly Ile Lys Gly His Lys Ala Gly
            195                 200                 205

Glu Glu Phe Thr Ile Asp Val Thr Phe Pro Glu Glu Tyr His Ala Glu
        210                 215                 220

Asn Leu Lys Gly Lys Ala Ala Lys Phe Ala Ile Asn Leu Lys Lys Val
225                 230                 235                 240

Glu Glu Arg Glu Leu Pro Glu Leu Thr Ala Glu Phe Ile Lys Arg Phe
                245                 250                 255

Gly Val Glu Asp Gly Ser Val Glu Gly Leu Arg Ala Glu Val Arg Lys
                260                 265                 270

Asn Met Glu Arg Glu Leu Arg Ala Pro Ser Val Thr Ala Leu Ser Ser
            275                 280                 285

Gln Ala Ile Glu Gly Leu Val Lys Ala Asn Asp Ile Asp Val Pro Ala
        290                 295                 300

Ala Leu Ile Asp Ser Glu Ile Asp Val Leu Arg Arg Gln Ala Ala Gln
305                 310                 315                 320

Arg Phe Gly Gly Asn Glu Lys Gln Ala Leu Glu Leu Pro Arg Glu Leu
                325                 330                 335

Phe Glu Glu Gln Ala Lys Arg Arg Val Val Val Gly Leu Leu Leu Gly
                340                 345                 350

Glu Val Ile Arg Thr Asn Glu Leu Lys Ala Asp Glu Glu Arg Val Lys
            355                 360                 365

Gly Leu Ile Glu Glu Met Ala Ser Ala Tyr Glu Asp Pro Lys Glu Val
        370                 375                 380
```

```
Ile Glu Phe Tyr Ser Lys Asn Lys Glu Leu Met Asp Asn Met Arg Asn
385                 390                 395                 400

Val Ala Leu Glu Glu Gln Ala Val Glu Ala Val Leu Ala Lys Ala Lys
                405                 410                 415

Val Thr Glu Lys Glu Thr Thr Phe Asn Glu Leu Met Asn Gln Gln Ala
                420                 425                 430

<210> SEQ ID NO 3
<211> LENGTH: 37
<212> TYPE: PRT
<213> ORGANISM: Escherichia coli

<400> SEQUENCE: 3

Phe Thr Gln His Asn Ala Leu Asn Ser His Lys Gly Pro Ser Pro Pro
 1               5                  10                  15

Gly Gly Gly Leu Phe Phe Val Met Asn Phe Ala Trp Asn Arg Ala Lys
                20                  25                  30

Ser Leu Phe Arg Cys
            35

<210> SEQ ID NO 4
<211> LENGTH: 72
<212> TYPE: PRT
<213> ORGANISM: Escherichia coli

<400> SEQUENCE: 4

Arg Asn Asn Lys Arg Leu Leu Cys Leu Lys Tyr Gly Asp Ala Val Pro
 1               5                  10                  15

Ile Thr Gln Gly Leu Ala Asp Asn Pro Ser Ile Arg Leu Gln Ser Val
                20                  25                  30

Gln Gln Val Phe Ser Ile Leu Ser Arg Arg Arg Lys Cys His Thr Ala
            35                  40                  45

Ala Asn Glu Ile Thr Leu His Pro Ile Trp Arg Trp Cys Arg Trp Ser
        50                  55                  60

Leu Asn Arg Pro Pro Arg Gly Glu
65                  70
```